United States Patent [19]

Siri

[11] Plant 5,218

[45] Apr. 10, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,116

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation having good branching and bud count, with sparkling white blossoms.

2 Drawing Figures

BACKGROUND OF THE NEW PLANT

This invention comprises a new and distinct miniature carnation variety that has its own set of characteristics that set it apart from all other varieties of miniature carnations. The newly discovered variety, called "Improved White Royalette," originated as a sport of White Royalette, an unpatented variety.

The botanical classification of the new variety is *Dianthus caryophyllus longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
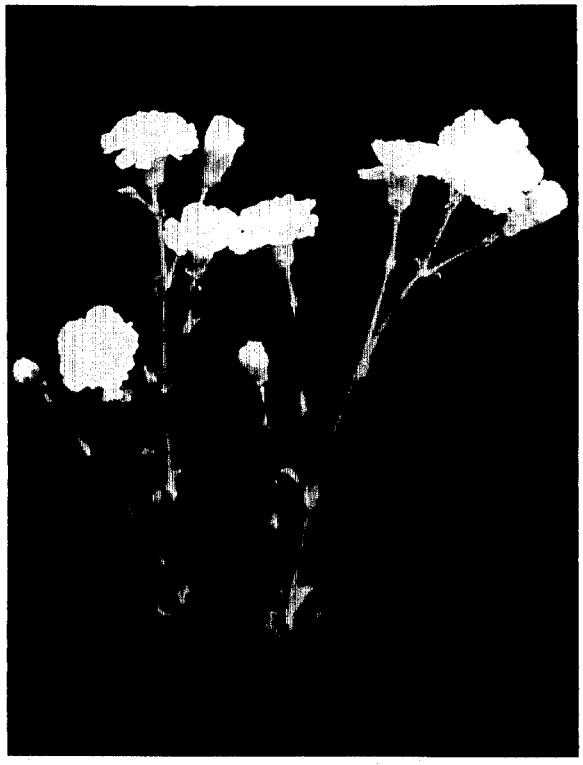
FIG. 1. PRIOR ART
FIG. 1 shows the sprays and stems of the new variety Improved White Royalette on the right and the prior White Royalette on the left.
Figure 2:
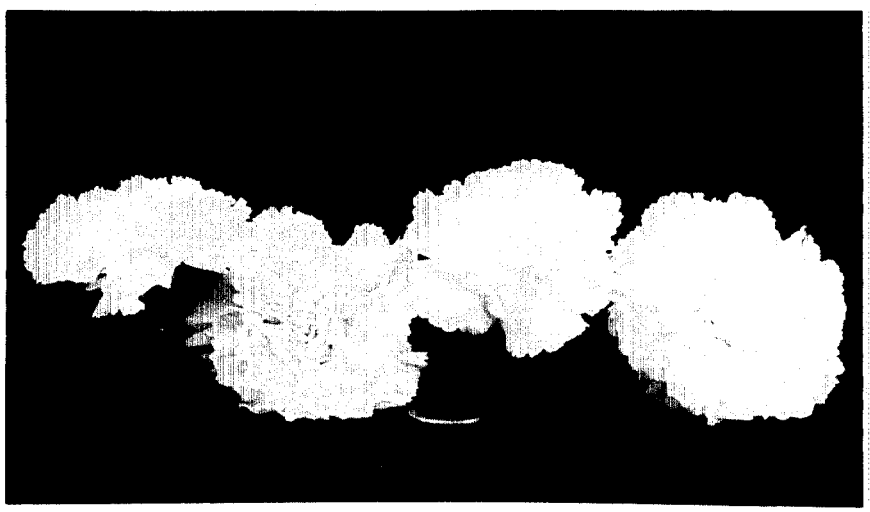
FIG. 2 shows the blooms of the new variety Improved White Royalette on the right and the prior White Royalette on the left.

The following detailed description of the new variety is based on my detailed observations of the new cultivar which were made at Siri Brothers Nursery Inc. at 940 O'Connor St., East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore Md. and "RHS" for Royal Horticultural Colour Chart, The Royal Horticultural Society, London, England.

GROWTH HABITS

Height: High as compared with other varieties.

Foliage: Average but less than parent.

Speed of growth: Average.

Root system: Average.

FOLIAGE

Leaf size:

*Length.*—Averages 4¼" at mid-stem.

*Width.*—Averages ⅜" at mid-stem.

Leaf shape: Average curl with a long acuminating tip.

Leaf texture: Smooth and leathery.

Leaf color:

Upperside.—RHS Green Group 139A with a whitish color over the green.

*Underside.*—RHS Green Group 139A with a whitish color over the green.

Leaf ribs: One rib down the center from the base to the tip of the leaf.

Leaf habit: Average amount of curl.

Leaf density: Average but less than parent which has heavy density.

STEM

Stem strength: Excellent, above average.

Stem color: RHS Green Group 139A with a whitish color over the green.

Nodes: Large.

*Space between nodes.*—3 inches average at midstem.

Stem branching: Excellent, better than parent.

BUDS

Bud shape: Oval.

Bud color: Top half LCC H-22 L-12 bottom half LCC H-22 L-10.

Average number of flowering buds per stem: 4–5.

Uniformity of bud opening: Very uniform.

Bud splitting: Very seldom.

Number of sepals per calyx: 70% of calyxs have 6; 20% of calyxs have 5; 10% of calyxs have 7.

FLOWER

Description of the color of the bloom: It is a pure slightly dirty white, not a bright white but a very clear white. There is an occasional fleck of purple at random on the bloom. However this does not appear often. The color of the fleck is H-43.

General tonality of the color: Clear and subdued.

Diameter of average bloom: 2¼ inches slightly larger than the parent.

Bloom shape: Generally round with a high center and flat outer petals.
Keeping quality: Average.
Fragrance: Very fragrant — above average.

PETALAGE

Petal texture: Soft and Velvety.
Petal edge: Medium serration.
Petal color: White RHS White Group 155B, with an occasional dark purple fleck LCC H-43 L-14, lighter or purple fleck LCC H-43 L-11.
Color stability: Excellent. There is only a slight reversion to the parent.
Petal size:
*Average length.*—1-9/16 inches.
*Average width at widest point.*—1 inch.
Calyx color: Top half LCC H-22 L-12, the bottom half is LCC H-22 L-10, the tips of the leaves on the bottom of the calyx are LCC H-19 L-15.

REPRODUCTIVE ORGANS

Stamen: With and without anthers.
Average length of stamen: 15/16 of an inch both with anthers and without.
Color of anthers: LCC H-48 L-6.
Color of filament: LCC H-22 L-1 is the color that is closest. The color is transparent.
Pistils:
*Shape.*—Approximately all the pistils have 2 styles.
*Number.*—One.
*Length from tip to ovary.*—Averages ¾ of an inch.
Stigma:
*Shape.*—Round located at the very tip of the style.
*Color.*—White.
Style:
*Color.*—LCC H-25 L-1.
Ovary:
*Shape.*—Ovid.
*Color.*—Tip LCC H-26 L-11, middle LCC H-22 L-4, bottom LCC H-23 L-1.
*Length.*—5/16 of an inch.
*Width.*—3/16 of an inch.

DISTINGUISHING CHARACTERISTICS BETWEEN THE NEW VARIETY AND PARENT

The leaf density of the Improved White Royalette is less than its parent. The Improved White Royalette is not as clubby and has better branching than its parent. The distance between the nodes is greater in Improved White Royalette than in its parent by an average of 1¼ inches. The Improved White Royalette has a better bud count than its parent, it has more fives. The white color is whiter and clearer in Improved White Royalette than in its parent. There are a lot less purple flecks in Improved White Royalette than in its parent. Improved White Royalette is a taller grower than its parent.

SIMILAR CHARACTERISTICS OF THE NEW VARIETY AND PARENT

All of the characteristics of both varieties are similar except for the distinguishing characteristics referred to above.

I claim:

1. A new and distinct variety of miniature carnation plant, substantially as herein shown and described.

* * * * *

PRIOR ART